(12) United States Patent
Tsur

(10) Patent No.: US 8,197,755 B2
(45) Date of Patent: Jun. 12, 2012

(54) INDICATOR STRIP AND A DEVICE FOR AUTOMATIC TESTING OF LIQUIDS

(76) Inventor: Ben David Tsur, Ramat Hasharon (IL)

( * ) Notice: Subject to any disclaimer, the term of this patent is extended or adjusted under 35 U.S.C. 154(b) by 616 days.

(21) Appl. No.: 11/631,375

(22) PCT Filed: Jul. 4, 2005

(86) PCT No.: PCT/IL2005/000706
§ 371 (c)(1),
(2), (4) Date: Apr. 16, 2008

(87) PCT Pub. No.: WO2006/003657
PCT Pub. Date: Jan. 12, 2006

(65) Prior Publication Data
US 2008/0193331 A1    Aug. 14, 2008

(30) Foreign Application Priority Data
Jul. 4, 2004    (IL) .......................................... 162842

(51) Int. Cl.
*G01N 21/00* (2006.01)
*G01N 31/00* (2006.01)
*G01N 33/00* (2006.01)
*G01N 21/75* (2006.01)
*G01N 31/22* (2006.01)
*G01N 33/52* (2006.01)
*G01N 35/00* (2006.01)
*G01N 21/77* (2006.01)

(52) U.S. Cl. ......... 422/66; 422/82.05; 422/420; 436/44; 436/169

(58) Field of Classification Search .................... 436/44; 422/66
See application file for complete search history.

(56) References Cited

U.S. PATENT DOCUMENTS

| | | | | |
|---|---|---|---|---|
| 4,218,421 A | * | 8/1980 | Mack et al. ...................... | 422/66 |
| 5,120,506 A | * | 6/1992 | Saito et al. ...................... | 422/66 |
| 5,169,600 A | * | 12/1992 | Ishizaka et al. ................. | 422/66 |
| 5,508,200 A | * | 4/1996 | Tiffany et al. ................... | 436/44 |
| 5,841,896 A | | 11/1998 | Tsuchiya | |
| 6,027,689 A | | 2/2000 | Markart | |
| 6,322,750 B1 | | 11/2001 | Barclay | |
| 6,436,698 B2 | * | 8/2002 | Park et al. .................. | 435/286.1 |
| 6,656,745 B1 | | 12/2003 | Cole | |
| 6,673,630 B2 | * | 1/2004 | Albarella et al. ............. | 436/518 |
| 2003/0207441 A1 | * | 11/2003 | Eyster et al. ................ | 435/287.1 |
| 2004/0053418 A1 | * | 3/2004 | Fouillet et al. ................ | 436/164 |

FOREIGN PATENT DOCUMENTS

| | | |
|---|---|---|
| DE | 19849539 | 5/2000 |
| EP | 1488736 | 12/2004 |
| WO | 2005/034740 | 4/2005 |

OTHER PUBLICATIONS

Office Action for Chinese Patent Application No. 200580022243.4, dated Dec. 7, 2011.

* cited by examiner

*Primary Examiner* — Jill Warden
*Assistant Examiner* — Charles D Hammond
(74) *Attorney, Agent, or Firm* — Bachman & LaPointe, P.C.

(57) ABSTRACT

A continuous indicator strip having a multiplicity of separate individual sequential test sections along the surface thereof, wherein a plurality of test sections are impregnated with the same indicator enabling the utilization of the strip for sequential repetitive testing of samples, the strip being provided with at least 20 such test sections.

5 Claims, 3 Drawing Sheets

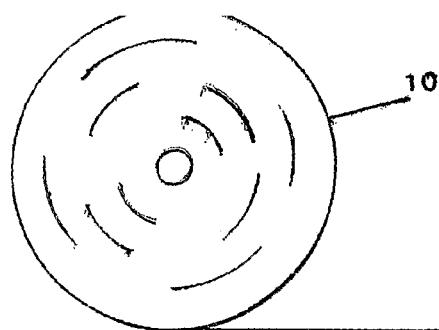
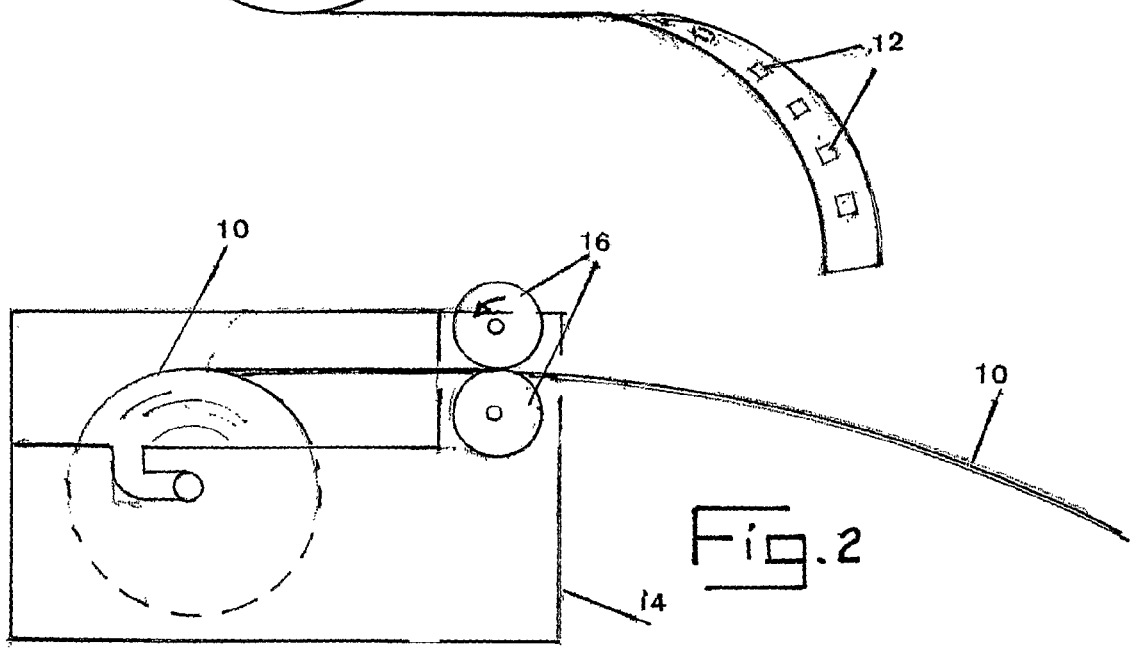
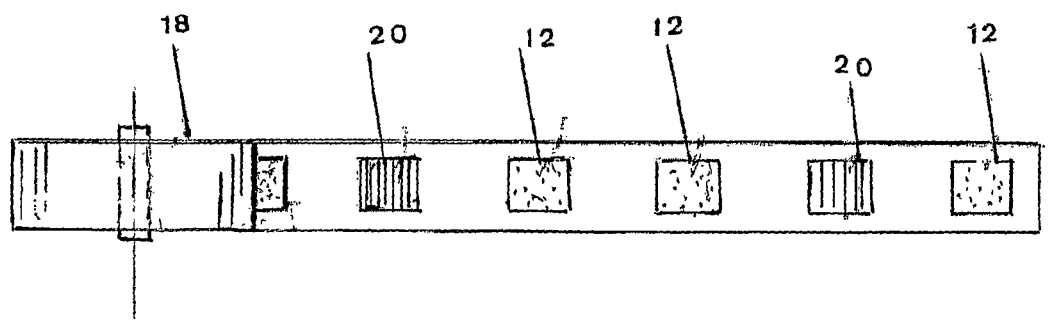

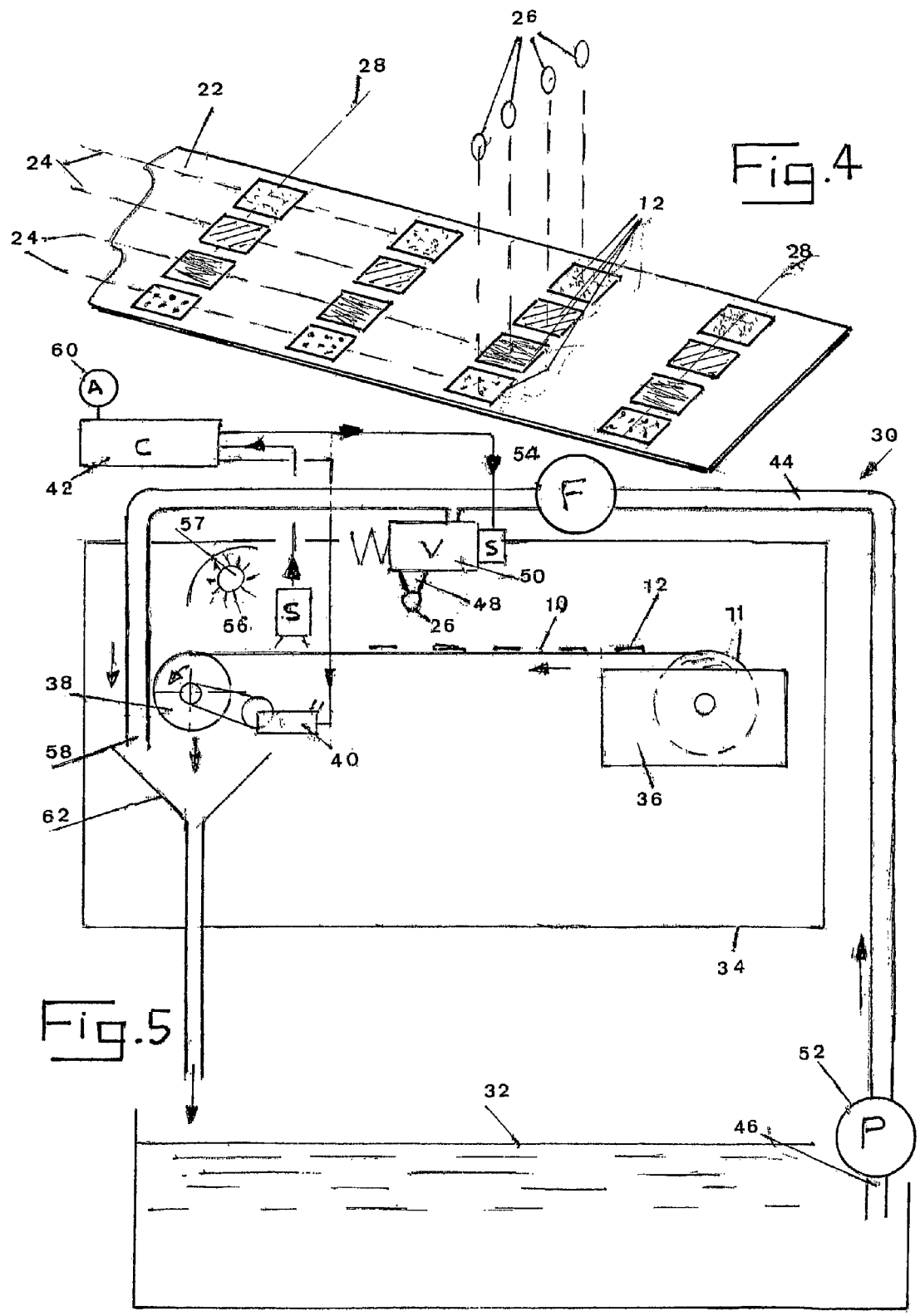

INDICATOR STRIP AND A DEVICE FOR AUTOMATIC TESTING OF LIQUIDS

BACKGROUND OF THE INVENTION

The present invention relates to the monitoring of substances entrained or dissolved in a liquid. More particularly, the invention provides a continuous tape carrying many test stations for sequential repetitive testing of samples of a liquid, typically water, taken from a swimming pool or reservoir where the substance in said liquid may either be desirable, for example chlorine in a swimming pool, or undesirable, for example an excess of sulfates, chlorides, nitrates and magnesium in a reservoir supplying drinking water.

The present specification deals primarily with chemical indicator strips, as opposed to thermal and stress indicator strips. Indicator strips are a known and used tool for determining if a chemical is present in a defined space or in a liquid of interest. The tape is exposed to the substance to be tested, and the color changes seen in the tape are indicative that such chemical is or is not present above a predefined level. For example, a strip used to monitor a reservoir holding drinking water could indicate whether the water contains the desired level of fluoride, and/or whether the water is within a defined range for the pH value.

Indicator strips are usually supplied in short lengths, and testing is carried out manually. Manual testing is suitable for applications where testing needs to be carried out only once or twice a day. However due to government or municipality regulations it is sometimes required to carry out frequent tests and in some situations even to provide proof that such tests were carried out and that the test results indicate that the substance of interest was present within an allowed concentration range. When many sequential tests are needed, manual test execution is tiresome and unreliable, and automatic testing is the best option.

The state of the art regarding indicator strips can be surmised from a review of recent US patents.

In U.S. Pat. No. 5,841,896 Tsuchiya discloses an apparatus for displaying the hue of a signal by using an indicator strip carrying printed indicia to indicate various hues.

Markart proposes a discrete test card in U.S. Pat. No. 6,027,689, useful primarily in the testing of body fluids. The card can be divided into individual test sections.

The indicator strip proposed by Barclay in U.S. Pat. No. 6,322,750 is responsive to gases, particularly hydrogen sulfide.

Cole discloses a multi-level semi-quantitative immunodiffusion assay in U.S. Pat. No. 6,656,745. While used for analysis, the device is not in the form of a tape.

A color-based system for automatic continuous effluent analysis is described by McNab, Incorporated, on the company's web site. However the system does not employ a continuous indicator tape.

For repetitive tests manual methods using discrete pieces of indicator tape are laborious and inconvenient, particularly when testing is required at fixed times around the clock.

It is therefore one of the objects of the present invention to obviate the disadvantages of prior art indicator tapes and arrangements for their deployment and to provide a testing system for liquids which is automatic and suitable for executing frequent tests.

SUMMARY OF THE INVENTION

The present invention achieves the above object by providing a continuous indicator strip having a multiplicity of separate individual sequential test sections along the surface thereof, wherein a plurality of said test sections are impregnated with the same indicator enabling the utilization of said strip for sequential repetitive testing of samples, said strip being provided with at least 20 such test sections.

In a preferred embodiment of the present invention there is provided a device for automated chemical testing of liquid samples, said device comprising a housing containing:

a) a continuous indicator strip in combination with a dispenser for holding and feeding said strip;

b) a take-up spool electrically driven for drawing said strip from said dispenser;

c) a liquid feed outlet above the path of said strip in combination with a solenoid-operated valve for sequentially dispensing drops of sample liquid onto said indicator strip;

d) an electro-optical sensor positioned to detect color changes in said test sections occurring as a result of contact with a drop of said sample liquid; and e) a controller unit connected to said sensor for noting and recording said changes.

In a most preferred embodiment of the present invention there is provided a device for monitoring the chemical characteristics of a body of water, particularly a swimming pool, said device further comprising a fluid circuit having an inlet positioned within the water of said body of water, a minor outlet connected to an inlet of said solenoid-operated valve, a major outlet, and pumping means to circulate said liquid in said circuit.

When more than one substance in the liquid needs to be monitored, the invention provides a dispenser for use in a device containing a plurality of continuous indicator strips and adapted to simultaneously hold and feed said plurality of strips adjacent to each other in a path below said liquid feed outlet in order to enable the utilization of said plurality of strips for sequential repetitive testing for various chemicals contained in a plurality of drops simultaneously delivered on each of said plurality of adjacent strips.

Yet further embodiments of the invention will be described hereinafter.

It will thus be realized that the continuous indicator tape of the present invention is ideal for use in combination with automatic machinery for carrying out frequent tests, for example once every two hours continuously day and night, even when no human operator is in attendance. After analysis of the results, the indicator tape is dated and stored and can be used as evidence that required tests have been carried out and that the results showed compliance to standards or that corrective action was undertaken and that substances in the water or other liquid were again brought into compliance of standards and/or of regulations.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an elevational view of a preferred embodiment of the strip according to the invention in a dispensing cartridge;

FIG. 2 is an elevational view of a strip and dispensing cartridge supported in a holder;

FIG. 3 is a plan view of an embodiment including test sections for calibration of an automatic device;

FIG. 4 is a perspective view of a strip for repetitive testing for various chemicals;

FIG. 5 is a diagrammatic view of a device for automatic monitoring of a pool of water such as a reservoir or swimming pool; and FIG. 6 is a perspective view of a dispenser for use in a device which is to monitor fluid for four substances.

DETAILED DESCRIPTION

Figure 6:
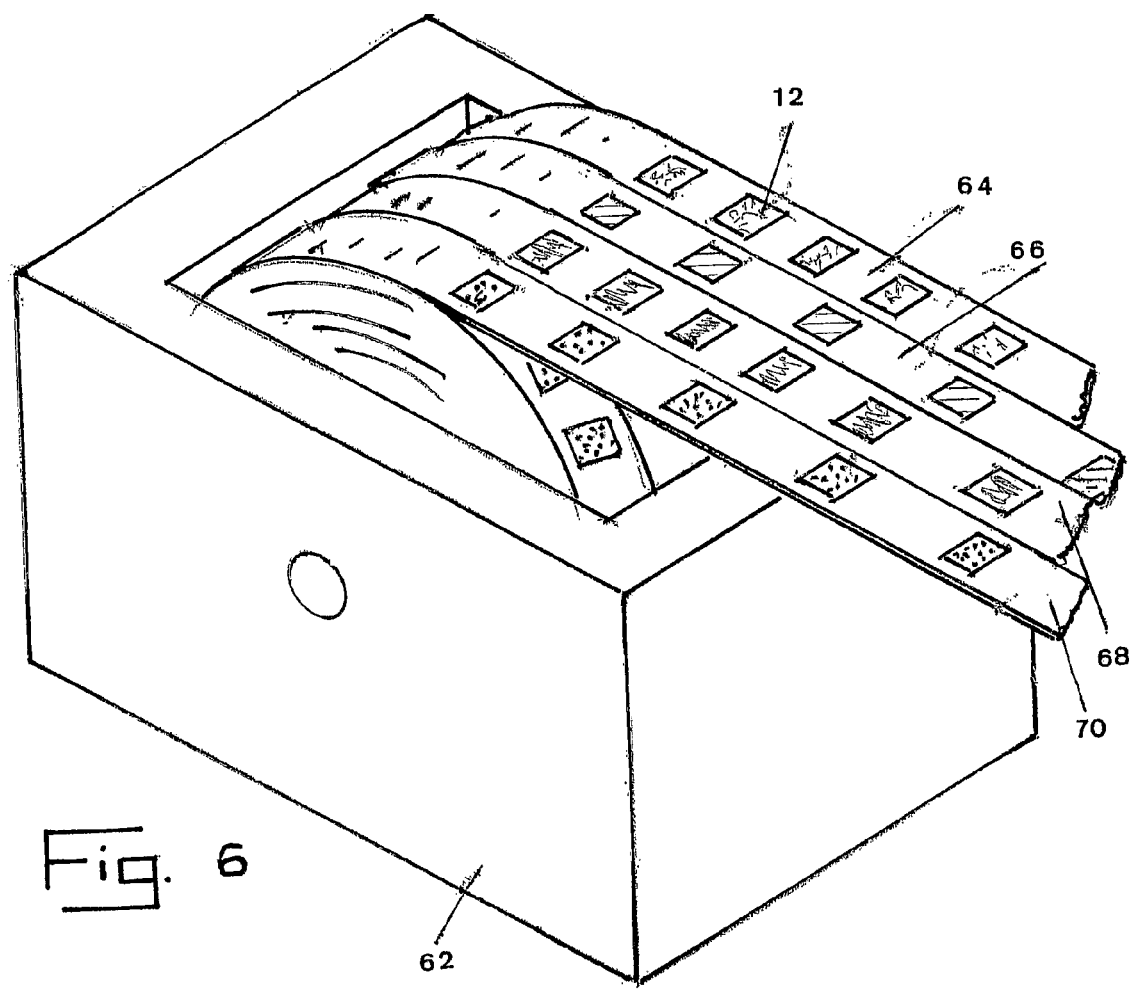

There is seen in FIG. 1 a continuous indicator strip 10 held in a dispensing cartridge 11 similar to those used for storing and dispensing 35 mm camera film. A multiplicity of separate individual sequential test sections 12 is disposed along the surface of said strip 10.

The test sections 12 are impregnated with a color-change agent sensitive to the substance of interest. The column of test sections enables the strip 10 to execute sequential repetitive testing of samples extracted at a predetermined time interval.

The strip is provided with at least 20, and preferably 40 or more such test sections.

Advantageously the strip is at least 30 cm in length and a desiccant (not shown) can be provided inside the cartridge 11.

With regard to the rest of the figures, similar reference numerals have been used to identify similar elements.

Referring now to FIG. 2, there is again seen the continuous indicator strip 10 previously described with reference to FIG. 1. The strip 10 and its storage cartridge 11 are inserted into and held in a dispenser 14 for holding and feeding the strip to a testing area (seen in FIG. 5). Although the strip 10 can be advanced manually, a pair of electrically driven pinch rollers 16 are arranged to advance the strip one pitch after each test. If testing is to be very frequent the strip can be advanced continuously at a velocity calculated to accord with the pitch of the test stations 12 and the number of tests to be carried out per time period.

FIG. 3 illustrates a continuous indicator strip 18, further provided with colored sections 20 interposed between some of the separate individual sequential test sections 12. The colored sections 20 are chemically inert and serve for calibration of a sensor, seen in FIG. 5, connected to read the active test sections 12.

Seen in FIG. 4 is a continuous indicator strip 22, wherein four columns 24 of the test sections 12 are provided side by side. Each column 24 carries test sections impregnated with a different indicator, enabling the utilization of the strip 22 for sequential repetitive testing for substances to be monitored.

When in use four sample drops 26 are delivered at each row 28 of the test sections 12. As seen in the present embodiment, there are four columns 24 so 4 drops 26 of the water to be tested are dropped, one drop on each test section 12.

Referring now to FIG. 5, there is depicted a device 30 for automated chemical testing of liquid samples, the device 30 being particularly suitable for monitoring the chemical characteristics of a body of water 32, which can be for example a swimming pool or a drinking water reservoir.

A housing 34 contains and supports a dispenser 36 for holding and feeding the continuous indicator strip 10.

A strip take-up spool 38 is electrically driven, and draws the strip from the dispenser 36. The take-up drive 40 is preferably intermittent, being activated by a controller 42 between test cycles. A slow continuous drive can be used where testing is to be carried out very frequently.

A fluid circuit 44 has an inlet 46 positioned within the body of water 32, and feeds a liquid outlet nozzle 48 seen above the path of the strip 10.

A solenoid-operated valve 50 is used for sequentially taking fluid from the fluid circuit 44 and dispensing a drop(s) 26 thereof onto the indicator strip 10.

The arrangement is such that only the drop(s) to be delivered are taken from the fluid circuit and all non-taken fluid continues in circulation to assure that the next test sample of fluid is a fresh one.

The fluid circuit 44 is completed by a major outlet 58 returning the water to the body of water 32 and by pumping means 52 to circulate the liquid in the circuit 44. Preferably the circuit 44 also contains a filter 54 to prevent possible blockage of the solenoid-operated valve outlet nozzle 48. Drops of water 26 remaining on the strip are collected by a funnel 62 and returned to the body of water 32

An electro-optical sensor 56 is positioned to view and detect color changes in the test sections 12. A light source 57 provides consistent illumination of the sections 12. Color changes occurring as a result of contact with the drop 26 of the sample liquid are detected by the sensor 56 and reported to the controller 42.

The electronic control unit 42 is programmed for noting and recording the color changes, which indicate that a substance of interest was present at, or exceeding, a given concentration level.

The electronic control unit 42 can easily be programmed to sound an alarm 60 on registering an excess or a missing component. For example given that drinking water may not contain more than 1 mg barium per liter, the alarm 60 can be activated when this level is approached or exceeded.

Turning now to FIG. 6, a dispenser 62 is illustrated for use in a device similar to that seen in FIG. 5, to be used for monitoring the presence of four different substances.

The dispenser 62 holds four continuous discrete indicator strips 64,66,68,70 in the present example, each individually stored in its own cartridge 11. The dispenser 62 enables the utilization of the four strips for sequential repetitive testing for various chemicals contained in the four drops 26 seen in FIG. 4 simultaneously delivered, one drop 26 on each of the four adjacent strips.

The device simultaneously holds and feeds the four strips adjacent to each other in a path below four liquid feed outlet nozzles 48, one of which is seen in FIG. 5. The use of discrete strips is advantageous because each strip can be sent separately for the type of analysis appropriate thereto.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for automated monitoring of chemical characteristics of water, said device comprising:

at least one continuous indicator strip having a multiplicity of separate individual sequential test sections along the surface thereof, said strip including a multiplicity of chemically inert calibration sections interposed between some, but not all, of said multiplicity of test sections, each of said test sections being impregnated with a color change agent sensitive to a substance of interest for sequential repetitive testing of water samples for the presence of said substance of interest in combination with a dispenser for holding and feeding said at least one strip;

at least one take-up spool electrically driven for drawing said at least one strip from said dispenser;

at least one water feed outlet for sequentially dispensing drops of sample water onto test sections of said at least one strip;

at least one electro-optical sensor positioned to detect color changes in said test sections occurring as a result of contact with a drop of said sample water;

a controller unit connected to said at least one sensor for noting and recording said changes, and a fluid circuit to provide said sample water to said at least one water feed outlet, said fluid circuit comprising:

an inlet positioned within a body of water to be tested;

a first outlet supplying water to said at least one water feed outlet;

a second outlet for returning water to said body of water;

a funnel, downstream from said at least one electro-optical sensor and said first and second outlets, operative to collect water remaining on said strip and water from said second outlet and to return said water remaining on said strip and said water from said second outlet to said body of water; and a circulation pump.

2. A dispenser for use in a device according to claim 1, containing said at least one continuous indicator strip and adapted to simultaneously hold and feed said at least one continuous indicator strip in a path below said liquid feed outlet.

3. A device according to claim 1, wherein said multiplicity of test sections comprises at least 20 test sections.

4. A device according to claim 1, wherein said at least one electro-optical sensor is calibrated by said controller unit based on reading said calibration sections.

5. A device according to claim 1, wherein said fluid circuit also comprises a filter operative to prevent blockage of said at least one water feed outlet.

\* \* \* \* \*